United States Patent [19]
Byron et al.

[11] Patent Number: 5,190,029
[45] Date of Patent: Mar. 2, 1993

[54] FORMULATION FOR DELIVERY OF DRUGS BY METERED DOSE INHALERS WITH REDUCED OR NO CHLOROFLUOROCARBON CONTENT

[75] Inventors: Peter R. Byron; Richard N. Dalby, both of Richmond, Va.

[73] Assignee: Virginia Commonwealth University, Richmond, Va.

[21] Appl. No.: 721,698

[22] Filed: Jun. 26, 1991

Related U.S. Application Data

[62] Division of Ser. No. 655,668, Feb. 14, 1991.

[51] Int. Cl.$^5$ .............. A61K 9/12; A61M 11/00; C09K 3/30
[52] U.S. Cl. .............. 128/200.14; 128/200.23; 128/203.15; 128/203.23; 222/635; 252/305; 424/45; 424/46
[58] Field of Search .............. 252/305; 424/45, 46; 222/635; 128/203.15, 203.23, 200.14, 200.23

[56] References Cited

U.S. PATENT DOCUMENTS

| | | | |
|---|---|---|---|
| 3,137,416 | 6/1964 | Shepherd et al. | 252/305 X |
| 3,592,364 | 7/1971 | Thornton | 222/635 X |
| 3,825,159 | 7/1974 | Laauwe | 222/402.24 |
| 4,174,295 | 11/1979 | Bargigia et al. | 252/305 |
| 4,254,129 | 3/1981 | Carr et al. | 514/317 |
| 4,254,130 | 3/1981 | Carr et al. | 514/317 |
| 4,285,957 | 8/1981 | Carr et al. | 514/317 |
| 4,285,958 | 8/1981 | Carr et al. | 514/317 |
| 4,778,674 | 10/1988 | Gupte et al. | 424/45 |
| 4,860,685 | 8/1989 | Smith | 427/140 X |
| 4,894,387 | 1/1990 | Butina et al. | 514/415 |
| 4,985,234 | 1/1991 | Nakamura et al. | 424/45 |
| 5,068,099 | 11/1991 | Sramek | 424/47 |
| 5,098,603 | 3/1992 | Perlman | 252/305 |
| 5,126,123 | 6/1992 | Johnson | 424/45 |

FOREIGN PATENT DOCUMENTS 0372777 11/1989 European Pat. Off. .

OTHER PUBLICATIONS

Nelson et al.: "Alternative Formulation to Reduce CFC Use in U.S. Exempted and Excluded Aerosol Products", EPA-600/2-89-061, Nov. 1989.
Dalby et al.: "CFC Propellant Substitution: P-134a as a Potential Replacement for P-12 in MDI's", *Pharm. Tech.*, Mar., 1990.
Dalby & Byron, "Comparison of Output Particle Size Distributions from Pressurized Aerosols Formulated as Solutions and Suspensions", Pharm. Res. 5, 36–39 (1988).
British Pharmacopoeia, p. 875, Appendix XVIIC, A20-4-A207 (1988).
Nelson et al., Alternative Formulations to Reduce CFC use in U.S. EPA Contract No. 68-02-4286.

*Primary Examiner*—Richard D. Lovering
*Attorney, Agent, or Firm*—Whitham & Marhoefer

[57] ABSTRACT

Aerosol formulations for use in metered dose inhalers are disclosed which include 1,1,1,2-tetrafluoroethane alone and in combination with other compounds as well as various hydrocarbon blends. The density, vapor pressure, flame extension characteristics, dispersability of medicant, dissolvability of surfactant, respirable fraction, and compatibility elastomer seals for the aerosol formulations have been examined. The aerosol formulations are attractive alternatives to chlorofluorocarbon based aerosols since they do not deplete the ozone layer.

3 Claims, 9 Drawing Sheets

| Propellant | % of Initial Weight After 24h Immersion in Propellant$^b$ | | | | | | |
|---|---|---|---|---|---|---|---|
| | LDP$^a$ | Nitrile | Black Buna | White Buna | Chloro-butyl | Butyl | Neoprene |
| CFC-11 | 127 | 141 | 142 | 137 | 227 | 286 | 170 |
| CFC-12 | 110 | 106 | 106 | 105 | 125 | 136 | 111 |
| CFC-114 | 103 | 100 | 101 | 101 | 107 | 109 | 102 |
| Propane | 107 | 102 | 102 | 102 | 109 | 117 | 104 |
| iso-Butane | 107 | 101 | 101 | 101 | 120 | 129 | 106 |
| n-Butane | 107 | 102 | 102 | 102 | 123 | 141 | 107 |
| HFC-134a | 101 | 117 | 112 | 114 | 100 | 101 | 101 |
| HCFC-123 | 109 | 414 | 457 | 398 | 145 | 158 | 136 |
| DME | 105 | 135 | 133 | 135 | 110 | 120 | 120 |
| Perfluoro-propane | 100 | 100 | 100 | 100 | 100 | 100 | 100 |

$^a$ LDP = low density polyethylene.
$^b$ 100 represents no weight gain.

| High Pressure Component | Composition[a] %w/w | g/10ml[c] | Low Pressure Component | Composition[a] %w/w | g/10ml[c] | Blend[b] Density (g/ml) |
|---|---|---|---|---|---|---|
| HFC-134a | 100 | 12.2 | None | 0 | 0 | 1.22 |
| HFC-134a | 99 | 12.1 | Ethanol (95%) | 1 | 0.1 | 1.22 |
| HFC-134a | 56 | 5.2 | iso-Butane | 44 | 4.1 | 0.93 |
| HFC-134a | 68 | 6.9 | n-Butane | 32 | 3.3 | 1.01 |
| HFC-134a | 58 | 7.7 | CFC-11 | 42 | 5.7 | 1.33 |
| HFC-134a | 56 | 7.5 | HCFC-123 | 44 | 5.8 | 1.33 |
| HFC-134a | 45 | 6.1 | CFC-114 | 55 | 7.5 | 1.36 |
| HFC-134a | 40 | 5.8 | Perfluoropentane | 60 | 8.8 | 1.45 |
| CFC-12 | 71 | 7.8 | iso-Butane | 29 | 3.3 | 1.10 |
| CFC-12 | 80 | 9.4 | n-Butane | 20 | 2.4 | 1.18 |
| CFC-12 | 72 | 9.9 | CFC-11 | 28 | 3.8 | 1.37 |
| CFC-12 | 71 | 9.7 | HCFC-123 | 29 | 4.0 | 1.37 |
| CFC-12 | 60 | 8.4 | CFC-114 | 40 | 5.5 | 1.38 |
| CFC-12 | 55 | 8.0 | Perfluoropentane | 45 | 6.5 | 1.45 |
| Propane | 22 | 1.2 | iso-Butane | 78 | 4.3 | 0.55 |
| Propane | 32 | 1.8 | n-Butane | 68 | 3.8 | 0.56 |
| Propane | 23 | 2.9 | CFC-11 | 77 | 9.6 | 1.26 |
| Propane | 22 | 2.8 | HCFC-123 | 78 | 9.8 | 1.25 |
| Propane | 15 | 2.0 | CFC-114 | 85 | 11.2 | 1.32 |
| Propane | 13 | 1.9 | Perfluoropentane | 87 | 12.8 | 1.46 |
| DME | 60 | 3.7 | iso-butane | 40 | 2.5 | 0.62 |
| DME | 72 | 4.6 | n-butane | 28 | 1.8 | 0.64 |
| DME | 62 | 6.0 | CFC-11 | 38 | 3.7 | 0.98 |
| DME | 60 | 5.9 | HCFC-123 | 40 | 3.9 | 0.98 |
| DME | 49 | 5.3 | CFC-114 | 51 | 5.5 | 1.07 |
| DME | 44 | 5.2 | Perfluoropentane | 56 | 6.7 | 1.19 |

[a] The composition of all propellant blends (except the first two) was calculated assuming all propellants behaved as ideal liquids and, therefore, obey Raoults law. Using this assumption it is possible to produce binary propellant blends of one low and one high pressure propellant with calculated vapor pressures of 67psia at 21°C, the calculated vapor pressure of 72%w/w CFC-12 and 28%w/w CFC-11.

[b] Density was calculated assuming ideal mixing.

[c] Actual propellant composition deviated from the nominal composition by an average of 0.4% and 6.1% (by weight) for the low and high pressure components, respectively.

FIG. 1

| Formulation | Density g/ml | | Visual Characterization | |
|---|---|---|---|---|
| | Calculated[a] | Measured[b] | Albuterol | Oleic Acid |
| HFC-134a | 1.22 | 1.22 | Floats/Dispersed | Part Dissolved |
| HFC-134a/Ethanol | 1.22 | 1.21 | Floats/Aggregated | Dissolved |
| HFC-134a/iso-Butane[c] | 0.96 | 0.76 | Sinks/Aggregated | Undissolved |
| HFC-134a/n-Butane[c] | 1.02 | 0.86 | Sinks/Dispersed | Dissolved |
| HFC-134a/CFC-11 | 1.33 | 1.31 | Floats/Dispersed | Dissolved |
| HFC-134a/HCFC-123 | 1.32 | 1.32 | Floats/Aggregated | Dissolved |
| HFC-134a/CFC114 | 1.35 | 1.33 | Adhered to OA | Undissolved |
| HFC-134a/Perfluoro-pentane | 1.44 | 1.41 | Floats/Aggregated | Undissolved |
| CFC-12/iso-Butane | 1.10 | 1.00 | Sinks/Dispersed | Dissolved |
| CFC-12/n-Butane | 1.17 | 0.83 | Sinks/Dispersed | Dissolved |
| CFC-12/CFC-11 | 1.37 | 1.27 | Floats/Dispersed | Dissolved |
| CFC-12/HCFC-123 | 1.37 | 1.43 | Floats/Dispersed | Dissolved |
| CFC-12/CFC-114 | 1.38 | 1.36 | Floats/Aggregated | Dissolved |
| CFC-12/Perfluoro-pentane | 1.45 | 1.50 | Floats/Dispersed | Undissolved |
| Proprane/iso-Butane | 0.55 | 0.54 | Sinks/Dispersed | Dissolved |
| Propane/n-Butane | 0.56 | 0.55 | Sinks/Dispersed | Dissolved |
| Propane/CFC-11 | 1.25 | 1.03 | Sinks/Dispersed | Dissolved |
| Propane/HCFC-123 | 1.25 | 1.04 | Sinks/Dispersed | Dissolved |
| Propane/CFC-114 | 1.30 | 1.13 | Suspended/Dispersed | Undissolved |
| Propane/Perfluoro-pentane [c] | 1.47 | 1.21 | Floats/Dispersed | Undissolved |
| DME/iso-butane | 0.62 | 0.61 | Sinks/Dispersed | Dissolved |
| DME/n-butane | 0.64 | 0.63 | Sinks/Dispersed | Dissolved |
| DME/CFC-11 | 0.98 | 0.85 | Sinks/Dispersed | Dissolved |
| DME/HCFC-123 | | 0.86 | NP | NP |
| DME/CFC-114 | 1.07 | 0.92 | Sinks/Dispersed | Dissolved |
| DME/Perfluoro-pentane[c] | 1.19 | 0.80 | Sinks/Aggregated | Dissolved |

[a] Density at 21°C was calculated from the actual weight of propellant used to prepare each blend, assuming ideal mixing.
[b] Measured at 21°C.
[c] Propellant separated into two liquid phases when cooled in dry ice/methanol.

FIG. 2

| Formulation | Vapor Pressure (psia) | |
|---|---|---|
| | Calculated[a] | Measured[b] |
| HFC-134a | 95.7 | 100 |
| HFC-134a/Ethanol | 95.7 | 105 |
| HFC-134a/iso-Butane | 68.8 | 110 |
| HFC-134a/n-Butane | 66.9 | 95 |
| HFC-134a/CFC-11 | 66.9 | 80 |
| HFC-134a/HCFC-123 | 69.8 | 65 |
| HFC-134a/CFC-114 | 67.8 | 80 |
| HFC-134a/Perfluoro-pentane | 69.1 | 80 |
| CFC-12/iso-Butane | 66.5 | 75 |
| CFC-12/n-Butane | 66.2 | 70 |
| CFC-12/CFC-11 | 67.2 | 70 |
| CFC-12/HCFC-123 | 66.5 | 70 |
| CFC-12/CFC-114 | 66.7 | 80 |
| CFC-12/Perfluoro-pentane | 67.2 | 65 |
| Propane/iso-Butane | 67.1 | 70 |
| Propane/n-Butane | 66.2 | 65 |
| Propane/CFC-11 | 71.4 | 80 |
| Propane/HCFC-123 | 66.2 | ND[c] |
| Propane/CFC-114 | 70.3 | 80 |
| Propane/Perfluoro-pentane | 65.9 | 95 |
| DME/iso-butane | 66.7 | 80 |
| DME/n-butane | 67.4 | 75 |
| DME/CFC-11 | 66.9 | 65 |
| DME/HCFC-123 | NP[d] | NP |
| DME/CFC-114 | 66.5 | 70 |
| DME/Perfluoro-pentane | 66.3 | 85 |

[a] Vapor pressure at 21°C was calculated from the actual weight of propellant used to prepare each blend, assuming ideal behavior.
[b] Pressures are reported to the nearest 5psi at 23°C.
[c] ND = not determined due to valve blockage.
[d] NP = not prepared due to valve blockage.

FIG. 3

| Propellant | Formula | Molecular Weight | Vapor[a] Pressure psia (21°C) | Density[a] g/ml (21°C) |
|---|---|---|---|---|
| High Pressure Propellants[b] (>67psia) | | | | |
| HFC-134a[c] | $CH_2F-CF_3$ | 102.0 | 95.7 | 1.224 |
| Propane[d,f] | $CH_3-CH_2-CH_2$ | 44.1 | 122.7 | 0.509 |
| Dimethyl-ether (DME)[d,f] | $CH_3-O-CH_3$ | 46.1 | 77.7 | 0.661 |
| CFC-12[c] | $CCl_2F_2$ | 120.9 | 84.9 | 1.325 |
| Low Pressure Propellants (<67psia) | | | | |
| HCFC-123[c] | $CF_3-CHCl_2$ | 152.9 | 11.0 | 1.465 (25°C) |
| n-Butane[d,f] | $CH_3-(CH_2)_2-CH_3$ | 58.1 | 31.7 | 0.585 |
| iso-Butane[d,f] | $CH(CH_3)_3$ | 58.1 | 45.7 | 0.564 |
| CFC-11[c] | $CCl_3F$ | 137.4 | 13.3 | 1.485 |
| CFC-114[c] | $CClF_2-CClF_2$ | 170.9 | 27.3 | 1.468 |
| Perfluoro-Pentane[e] | $CF_3-(CF_2)_3-CF_3$ | 288 | 12.5 (25°C) | 1.604 (25°C) |

[a] Vapor pressure and density information was obtained from appropriate propellant supplier. Values are quoted at 21°C unless 25°C appears in parenthesis.
[b] High pressure propellants in this paper are defined as those exhibiting vapor pressures >67psia at 21°C.
[c] Du Pont, Willmington, DE.
[d] Phillips 66 Co., Bartlesville, OK.
[e] ISC Chemicals, Avonmouth, United Kingdom.
[f] Flammable at certain concentrations in air.

FIG. 4

| Formulation | Flame Extension (cm) |
|---|---|
| HFC-134a | Non-flammable |
| HFC-134a/Ethanol | Non-flammable |
| HFC-134a/iso-Butane | 20 |
| HFC-134a/n-Butane | 30 |
| HFC-134a/CFC-11 | Non-flammable |
| HFC-134a/HCFC-123 | Non-flammable |
| HFC-134a/CFC-114 | Non-flammable |
| HFC-134a/Perfluoropentane | Non-flammable |
| CFC-12/iso-Butane | 20 |
| CFC-12/n-Butane | 20 |
| CFC-12/CFC-11 | Non-flammable |
| CFC-12/HCFC-123 | Non-flammable |
| CFC-12/CFC-114 | Non-flammable |
| CFC-12/Perfluoropentane | Non-flammable |
| Propane/iso-Butane | 50 |
| Propane/n-Butane | 40 |
| Propane/CFC-11 | 20 |
| Propane/HCFC-123 | 20 |
| Propane/CFC-114 | 50 |
| Propane/Perfluoropentane | 40 |
| DME/iso-butane | 30 |
| DME/n-butane | 30 |
| DME/CFC-11 | 20 |
| DME/HCFC-123 | NP[a] |
| DME/CFC-114 | 20 |
| DME/Perfluoropentane | Non-flammable/15[b] |

[a] NP = not prepared due to valve blockage.
[b] During six repeat extension tests this formulation extinguished the propane torch twice, appeared non-flammable once and showed a flame extension of 15cm three times.

FIG. 5

| Formulation | Mean Shot Weight / Actuation (mg, n=10) | | Expected[a] Shot Wt. (mg) |
| --- | --- | --- | --- |
| | 1 Hour Post Crimping of Metering Valve | 24 Hours Post Crimping of Metering Valve | |
| HFC-134a | 81[b] | 76 | 77[c] |
| HFC-134a/iso-Butane | 51 | 50 | 48 |
| HFC-134a/n-Butane | 53 | 50 | 54 |
| HFC-134a/CFC-11 | 79 | 75 | 83 |
| CFC-12/iso-Butane | 57 | Failed to Fire | 63 |
| CFC-12/n-Butane | 70 | 65 | 52 |
| CFC-12/CFC-11 | 94 | 82 | 80 |
| CFC-12/HCFC-123 | 80 | Stiff 59 | 90 |
| Propane/iso-Butane | 34 | 32 | 34 |
| Propane/n-Butane | 33 | 33 | 35 |
| Propane/CFC-11 | 58 | 57 | 65 |
| Propane/HCFC-123 | 57 | Stiff 50 | 65 |
| DME/iso-butane | 35 | 37 | 38 |
| DME/n-butane | 38 | 37 | 40 |
| DME/CFC-11 | 47 | 44 | 54 |
| DME/CFC-114 | 55 | 54 | 58 |
| DME/Perfluoropentane | 58 | 59 | 50 |

[a] Expected shot weight = Density x 63 / 1000. Where Density is the measured propellant density, and 63ul is the volume of the metering valve.
[b] Valve operated smoothly and without unusual stiffness unless otherwise noted.
[c] ND = not determined

FIG. 6

| Formulation | Percentage Deposition in | | |
|---|---|---|---|
| | Actuator | Evaporation Chamber | Impactor |
| HFC-134a | 16 (2) | 40 (5) | 44 (6) |
| HFC-134a/n-Butane | 21 (2)[a] | 51 (4) | 27 (4) |
| HFC-134a/CFC-11 | 14 (1) | 65 (4) | 22 (3) |
| CFC-12/iso-Butane | 18 (1) | 48 (1) | 33 (1) |
| CFC-12/n-Butane | 17 (1) | 55 (2) | 28 (2) |
| CFC-12/CFC-11 | 20 (1) | 55 (4) | 26 (4) |
| CFC-12/HCFC-123 | 8[b] | 57 | 34 |
| Propane/iso-Butane | 20 (2) | 42 (4) | 39 (4) |
| Propane/n-Butane | 16 (3) | 55 (1) | 29 (1) |
| Propane/CFC-11 | 21 (1) | 46 (2) | 33 (1) |
| Propane/HCFC-123 | 22 (1) | 45 (2) | 34 (1) |
| DME/iso-butane | 18 (1) | 50 (2) | 32 (2) |
| DME/n-butane | 21 (1) | 47 (2) | 33 (2) |
| DME/CFC-11 | 23 (3) | 50 (4) | 27 (2) |
| DME/CFC-114 | 21 (0) | 51 (1) | 28 (1) |
| DME/Perfluoro-pentane | 18 (2) | 46 (5) | 36 (4) |

[a]Mean of 3 replicates. Value in parenthesis represents 0.5 x Range.

[b]MDI failed to fire after first cascade impaction experiment.

FIG. 7

| Propellant | % of Initial Weight After 24h Immersion in Propellant[b] | | | | | | |
|---|---|---|---|---|---|---|---|
| | LDP[a] | Nitrile | Black Buna | White Buna | Chloro-butyl | Butyl | Neoprene |
| CFC-11 | 127 | 141 | 142 | 137 | 227 | 286 | 170 |
| CFC-12 | 110 | 106 | 106 | 105 | 125 | 136 | 111 |
| CFC-114 | 103 | 100 | 101 | 101 | 107 | 109 | 102 |
| Propane | 107 | 102 | 102 | 102 | 109 | 117 | 104 |
| iso-Butane | 107 | 101 | 101 | 101 | 120 | 129 | 106 |
| n-Butane | 107 | 102 | 102 | 102 | 123 | 141 | 107 |
| HFC-134a | 101 | 117 | 112 | 114 | 100 | 101 | 101 |
| HCFC-123 | 109 | 414 | 457 | 398 | 145 | 158 | 136 |
| DME | 105 | 135 | 133 | 135 | 110 | 120 | 120 |
| Perfluoro-propane | 100 | 100 | 100 | 100 | 100 | 100 | 100 |

[a] LDP = low density polyethylene.
[b] 100 represents no weight gain.

FIG. 8

| Propellant | % Increase in Length of Nitrile Elastomer After 24h in Propellant | % Increase in Weight of Nitrile Elastomer After 24h in Propellant |
|---|---|---|
| CFC-11 | 10.7 | 40.1 |
| CFC-12 | 3.9 | 5.6 |
| CFC-114 | 4.0 | 0.8 |
| HCFC-123 | 52.9 | 293.3 |
| HFC-134a | 8.0 | 16.5 |
| Butane | 3.4 | 2.2 |
| Isobutane | 3.8 | 1.1 |
| Propane | 2.4 | 5.3 |
| Dimethylether | 15.9 | 30.6 |
| Perfluoropentane | -1.4 | 0.2 |

FIG. 9

FORMULATION FOR DELIVERY OF DRUGS BY METERED DOSE INHALERS WITH REDUCED OR NO CHLOROFLUOROCARBON CONTENT

CROSS REFERENCED TO RELATED APPLICATIONS

This application is a division of co-pending application Ser. No. 07/655,668, filed on Feb. 14, 1991 and is herein incorporated by reference.

BACKGROUND OF THE INVENTION

1. Field of the Invention

The present invention generally relates to propellant compositions used for delivering drugs to patients from metered dose inhalers and, more particularly, to propellant compositions which have reduced or no chlorofluorocarbon content such that their use is environmentally sound.

2. Description of the Prior Art

Metered dose inhalers (MDIs) are, at present, the most efficient and best-accepted means for accurately delivering drugs in small doses to the human respiratory tract. Therapeutic agents commonly delivered by the inhalation route include bronchodilators ($B_2$ agonists and anticholinergics), corticosteroids, and anti-allergics. Inhalation may also be a viable route for anti-infective, vaccinating, systemically acting and diagnostic agents, as well as anti-leukotrienes, and anti-proteases.

MDIs comprise a pressure resistant container typically filled with a product such as a drug dissolved in a liquified propellant or micronized particles suspended in a liquified propellant where the container is fitted with a metering valve. Actuation of the metering valve allows a small portion of the spray product to be released whereby the pressure of the liquified propellant carries the dissolved or micronized drug particles out of the container to the patient. The valve actuator is used to direct the aerosol spray into the patient's oropharynx. Surfactants are usually dissolved in the spray product and can serve the dual functions of lubricating the valve and reducing aggregation of micronized particles.

For many years the preferred propellants used in MDIs were a group of chlorofluorocarbons which are commonly called Freons or CFCs, such as $CCl_3F$ (Freon 11 or CFC-11), $CCl_2F_2$ (Freon 12 or CFC-12), and $CClF_2-CClF_2$ (Freon 114 or CFC-114). Often times the propellant used in the MDI is a blend of compounds and the combination of Freon 11, Freon 12, and Freon 114 has been in widespread use in the MDI industry for many years. Chlorofluorocarbons have qualities particularly suitable for use in MDIs including vapor pressures, densities, and elastomer swelling properties which provide respectively for optimal respirable fractions, enhanced suspension stability, and repeatable valve metering.

Recently, however, the use of chlorofluorocarbons per se has come under sharp attack because they are known to deplete stratospheric ozone. Hence, chlorofluorocarbons are considered to be extremely hazardous to the environment. Signatory countries to the *Montreal Protocol on Substances that Deplete the Ozone Layer*, have resolved to reduce the use of chlorofluorocarbons in a step-by-step fashion over the next ten years and ban their use altogether after the year 2000 a.d. No exemption has been made in the *Montreal Protocol* for the use of chlorofluorocarbons in MDIs. Therefore, identification of any alternative propellant system(s) which can be used in MDIs will provide an immediate benefit to the MDI industry, and the patients they serve.

Suitable propellant systems may be found in a large number of different classes of halogenated and non-halogenated hydrocarbons including: hydrochlorofluorocarbons (HCFCs) which are alkyl molecules with chloro, fluoro, and hydrogen moieties on the carbon backbone; hydrofluorocarbons (HFCs) which are alkyl molecules with fluoro and hydrogen moieties on the carbon backbone; hydrocarbons (HCs) which include alkane and alkene molecules having only hydrogen moieties on the carbon backbone; fluorocarbons (FCs) which are similar to the HCs except that fluorine moieties are on the carbon backbone instead of hydrogens; and several miscellaneous liquified propellants such as dimethyl ether and ethanol. Compressed gases such as carbon dioxide, nitrogen and nitrous oxide may also provide possible solutions. Propellant systems which use HCFCs are believed to only be temporary solutions because the ozone depleting potential of these compounds may still be a problem. The prior art is replete with examples of propellant systems which employ the above-noted types of compounds; however, few propellant systems have been discovered which are suitable alternatives to the use of chlorofluorocarbons in MDIs.

In the European Patent Application 0,372,777 of Riker Laboratories (hereinafter EP application), there are disclosed several self-propelling aerosol formulations which may be used in MDIs and which may be free from chlorofluorocarbons. The formulations discussed in the EP application comprise a medicament, 1,1,1,2-tetrafluoroethane (HFC-134a), a surface active agent, and an adjuvant compound having a higher polarity than 1,1,1,2-tetrafluoroethane. According to the EP application, the presence of an adjuvant compound of higher polarity than HFC-134a is a critical feature of the preparation of a stable, effective aerosol formulation and states that without a higher polarity adjuvant compound, HFC-134a would be an unsuitable propellant system for use in an MDI. The EP application states further that the preferred solubility parameter, which is somewhat dependent on propellant polarity, ranges between 6.5 and 7.8 $(cal/cm^3)^{\frac{1}{2}}$ and mixtures having a solubility parameter below 6.0 $(cal/cm^3)^{\frac{1}{2}}$ would be unacceptable. Vapor pressure is reported to preferably range between 40 and 90 psig and density is reported to preferably range between 1.0 and 1.5 $g/cm^3$. The EP application states that the preferred ratio of HFC-134a:-higher polarity adjuvant compound ranges between 85:15 and 95:5.

SUMMARY OF THE INVENTION

It is therefore an object of the present invention to provide propellant formulations for use in MDIs which have reduced or no chlorofluorocarbon content.

It is another object of this invention to provide propellant formulations for use in MDIs which are compatible with the elastomer seals that are positioned at the juncture of the pressurized container and the valve actuator.

It is another object of the present invention to provide formulations for use in MDIs which include a drug and a surfactant suspended in HFC-134a alone or in combination with other compounds such as perfluoropentane, propane, butane, and isobutane.

It is yet another object of the present invention to provide formulations for use in MDIs which primarily use hydrocarbon blends as the propellant.

According to the invention, experiments were conducted to reformulate a typical MDI product to reduce or eliminate the use of chlorofluorocarbons. In the experiments, micronized albuterol was used as the drug product and oleic acid was used as the surfactant, although those skilled in the art will recognize that the medicament and surfactant and their respective concentrations may be chosen and varied to suit the objective of drug deliver to the lungs of the patient. The ideal alternative propellant will satisfy the following criteria: (1) The propellant blend should consist of a single liquid phase at room temperature, (2) the surfactant (oleic acid) should dissolve in the propellant blend, (3) the micronized drug (albuterol) should be easily dispersible in the propellant blend with the aid of the surfactant (oleic acid), (4) the vapor pressure should range between 50 to 110 psia at 21° C., (5) the formulation may contain a low vapor pressure component to facilitate slurry preparation which is typically used for packaging MDI products, (6) the aerosolized drug (albuterol) particle size following spraying should be as small as possible to maximize penetration into the lung, and (7) the propellant blend should be compatible with existing valve components, elastomer seals and packaging equipment. The flammability of the propellant was considered for safety reasons, but is not considered to preclude use in an MDI as evidenced by the common use of flammable propellants in the hairspray and breath freshener industry.

The types of propellants examined included chlorofluorocarbons (CFC-11, 12 and 114), hydrochlorofluorocarbons ($CCl_2HCF_3$ which is commonly called HCFC-123), hydrofluorocarbons (HFC-134a), hydrocarbons (propane, n-butane and isobutane), fluorocarbons (perfluoropentane), dimethyl ether and ethanol. The CFC, HCFC and dimethyl ether propellants are commercially available from the E. I. DuPont De Nemours company of Delaware. The hydrocarbon propellants are commercially available from Phillips 66 Chemical company of Oklahoma. In the experiments, two component propellant blends and HFC-134a alone were evaluated in the presence of micronized albuterol and oleic acid. The results of the experiments reported herein include vapor pressure (which ranged between 65-110 psia at 23° C.), albuterol dispersion characteristics, oleic acid solubility, the number of liquid phases, density (which ranged between 0.39 and 1.34 g/ml at 21° C.), flame extension (which varied from 50 cm to non-flammable), product weight loss per actuation (which ranged between 33-94 mg per actuation), and the potentially respirable fraction (which ranged between 22-39% of output less than or equal to 11.2 $\mu$m in aerodynamic diameter).

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a table showing the weight of propellant used in several test formulations, these formulations also being referred to in FIGS. 2 through 6;

FIG. 2 is a table showing the density of several test formulations and the visual characterization of the albuterol and oleic acid components in the formulations;

FIG. 3 is a table showing the calculated and measured vapor pressures of several test formulations;

FIG. 4 is a table showing the molecular weight, vapor pressure, and density of the high pressure and the low pressure propellants used in the propellant blends;

FIG. 5 is a table showing the observed flame extension for several test formulations sprayed towards an open flame;

FIG. 6 is a table showing average shot weight per actuation at two different times for several test formulations which demonstrates the reproducibility of valve metering for the formulations;

FIG. 7 is a table showing the distribution of sprayed albuterol as determined by cascade impaction for the formulations;

FIG. 8 is a table showing the weight gain of particular elastomer seals after 24 hours of immersion in liquified propellants; and FIG. 9 is a table showing the nitrile elastomer swelling after 24 hours of immersion in liquified propellants.

DETAILED DESCRIPTION OF THE PREFERRED EMBODIMENTS OF THE INVENTION

Various experiments have been performed with several different test formulations in order to determine acceptable propellant systems which might be utilized in MDIs. The primary focus of the experiments was to determine suitable alternatives to the chlorofluorocarbon propellants that are presently in widespread use.

With reference to the drawings and, more particularly to FIG. 1, several different test formulations were prepared and, with the exception of the test formulation containing HFC-134a as the sole propellant (shown at the top of FIG. 1), each of these test formulations contained high and low pressure propellant components. The composition of all propellant blends was calculated with the assumption that all propellants behaved as ideal liquids which obey Raoult's law. Using this assumption, the objective was to produce binary (two component) propellant blends comprised of one high and one low pressure propellant with a calculated vapor pressure near 67 psia at 21° C, which is the calculated vapor pressure of the 72% w/w CFC-12 and 28% w/w CFC-11 blend used in several commercial MDI formulations. It should be understood that propellant blends with three or more components could similarly be prepared. Each test formulation was prepared by adding 32.3±0.2 mg of micronized albuterol and 20.2±0.3 mg of oleic acid to 10 ml of each propellant blend in a pressure resistant aerosol container. The aerosol containers were fitted with both continuous and metering valves using commercially available Pamasol small scale aerosol packaging equipment available from Pfaffikon of Switzerland. Suitable containers, valves and gaskets are commercially available from the Bespak company of North Carolina. The formulations were shaken and ultrasonicated for the purpose of dissolving the oleic acid and dispersing the albuterol. In addition to reporting the actual weight of each propellant in g/10 ml and the weight percentage of each propellant for each test formulation, FIG. 1 also reports the calculated blend density for the propellant compositions assuming ideal mixing. The vapor pressure, density, and molecular weight reported by the supplier of each propellant was used as the basis for all calculations.

In the following experiments discussed in conjunction with FIGS. 2–7, the response of the test formulations containing HFC-134a alone or HFC-134a in combination with perfluoropentane and isobutane are deemed to be particularly relevant. Rather than having a more polar adjuvant compound act in combination with HFC-134a as is stated to be critical in EP application 0,372,777 to aid in dissolving the surface acting agent and in dispersing the medicament, these formulations either have no adjuvant compound, as is the case where HFC-134a is utilized alone as the propellant, or have a low pressure component which has a solubility parameter that is less than HFC-134a (e.g., HFC-134a has a solubility parameter of 6.6 $(cal/cm^3)^{\frac{1}{2}}$ while perfluoropentane has a solubility parameter of 5.66 $(cal/cm^3)^{\frac{1}{2}}$ and isobutane has a solubility parameter of 6.17 $(cal/cm^3)^{\frac{1}{2}}$. In addition, the hydrocarbon based blends were also found to have particularly promising characteristics for use in MDIs.

FIG. 2 is a table showing the calculated and measured blend densities for all the test formulations as well as the results of a visual examination of each test formulation which was made within two days of preparing the aerosol unit. The calculated blend density at 21° C. was determined, as stated above, assuming ideal mixing and using the actual weight and reported densities of propellants in the blend indicated in FIG. 1. The measured blend density at 21° C. for the propellant blends was determined from blank formulations which did not contain albuterol or oleic acid using a densitometer. It should be understood that many solid drugs have densities which are similar in magnitude to albuterol.

While density is not dispositive of the utility of a propellant blend, mismatches between drug and propellant density can result in poor suspension stability. In the DME/isobutane (density=0.61 g/ml) and HFC-134a/perfluoropentane (density=1.41 g/ml) blends, rapid sinking and floating, respectively, resulted. If albuterol floats to the propellant surface due to a mismatch in density, a lower than expected dose is likely to be released during the first actuation following a period of quiescence. Surprisingly, albuterol sank to the bottom of the aerosol container relatively slowly in formulations containing the hydrocarbon propellant blends (which have relatively low densities). This property is highly desirable for MDI applications and might be the result of a high degree of particulate deaggregation, since small, individual particles are known to sediment more slowly than larger aggregates. The formulation which utilizes HFC-134a as the sole propellant and other HFC-134a based blends, which have calculated densities ranging between 1.2 and 1.4 g/ml, also had relatively stable suspensions.

In FIG. 2, albuterol which is described as "dispersed" easily produced a visually homogeneous, opaque suspension on gentle shaking, while that described as "aggregated" produced one or more large clumps suspended in liquified propellant or adhered to the glass container. While not specifically shown in FIG. 2, albuterol was relatively difficult to deaggregate in CFC based formulations, but was very easy to deaggregate in hydrocarbon based systems. In most hydrocarbon based formulations, the albuterol spontaneously dispersed. The observed ease of albuterol deaggregation in the hydrocarbon based formulations makes hydrocarbons attractive alternatives to CFCs because shorter mixing times or the complete absence of a need for homogenization would reduce manufacturing costs and complexity. The method of MDI preparation used in these investigations did not permit mechanical deaggregation of the micronized albuterol in the liquified propellant (i.e., there was no direct contact between a homogenizer head and aggregated particles of albuterol). In place of the high shear mixers and homogenizers which are commonly used in commercial filling operations, vigorous shaking and ultrasonication of individually filled MDIs was employed in order to conserve propellant. Despite these less forceful methods of mixing, in most cases a product was produced that was judged by visual inspection to be dispersed and deaggregated. In view of the above, it is possible that some formulations reported in FIG. 2 which are identified as "aggregated" could have benefitted from a dispersion technique that involved mechanical deaggregation of albuterol aggregates.

In most of the test formulations, oleic acid was a viable surfactant and dissolved completely at ambient temperature. The concentration of oleic acid used in these studies (20 mg/10 ml or 0.2% weight in volume (w/v)) represents a high surfactant concentration compared to the concentration used in several commercially available MDI products. Therefore, some of the formulations identified as containing "undissolved" oleic acid may still be useful in formulations which require reduced surfactant levels. For example, in the formulation containing HFC-134a as the sole propellant, oleic acid was only partly dissolved after shaking; however, the large amount of oleic acid used in the experiments may not actually be required in a typical MDI application and thus a suitable formulation in HFC-134a alone would simply employ a lower concentration of entirely dissolved oleic acid. In addition, other surfactants utilized in commercial MDIs (e.g., sorbitan trioleate and soya lecithin), are known to exhibit different solubility characteristics and may be suitable for use with propellant blends in which oleic acid failed to dissolve.

All the propellant blends investigated displayed a single liquid phase at ambient temperature which is a very important characteristic of any propellant system which will be used in a metered dose inhaler environment (patients use MDIs at room temperature). Most of the propellant blends also remained as a single phase on cooling with dry ice/methanol; however, the dimethyl ether (DME)/perfluoropentane blend separated into two liquid phases when cooled in dry ice/methanol. Separation into two liquid phases at low temperature would severely limit the utility of such a blend in a cold filling operation, although the same blend may be amenable to pressure filling.

FIG. 3 is a table showing the calculated vapor pressure of the test formulations at 21° C. where the calculations were made assuming ideal behavior, and the measured vapor pressure at 23° C. for the test formulations (vapor pressure was measured using a calibrated gauge). Many of the propellant blends investigated yielded vapor pressures close to the expected value (65-85 psia at 23° C.). Hence, the vapor pressure experiment demonstrates that it is possible to achieve vapor pressures similar to those encountered in current CFC based MDIs using alternative propellants. In most cases the measured pressure exceeded the calculated pressure. The most striking differences between calculated and measured vapor pressures were observed in blends containing HFC-134a and a hydrocarbon propellant wherein the formulations showed a vapor pressure more than 40% higher than expected. The 2° C. temperature difference between the calculated pressure and the measured pressure cannot account for this large variance. In addition, the propane and DME blends mixed with the low pressure perfluoropentane component also showed a vapor pressure approximately 30% higher than expected. Large pressure differences such as these are indicative of a positive deviation from Raoult's law and are probably indicative of little intermolecular bonding between dissimilar propellant molecules.

FIG. 4, with reference back to FIG. 3, shows that with the exception of the formulation containing only HFC-134a as the propellant, all MDIs contained a low pressure component which would facilitate slurry formation. High pressure propellants are herein defined as those exhibiting vapor pressures greater than 67 psia at 21° C. and low pressure propellants are herein defined as those exhibiting vapor pressures less than 67 psia at 21° C. (or 25° C. as in the case of perfluoropentane). The molecular weight, vapor pressure and density information reported in FIG. 4 were obtained from the propellant suppliers and the values are quoted at 21° C. unless 25° C. appears in parenthesis. Because of the presence of the low pressure component, it is likely that all test formulations, except the formulation containing HFC-134a alone, could be filled using conventional cold or pressure filling technology. To fill products containing HFC-134a, which has a boiling point of −26° C., as the sole propellant, may require a different approach, such as pressure filling the premixed suspension in a single stage process.

FIG. 5 is a table showing the observed flame extension for the test formulations. Flame extension was measured by firing each MDI horizontally from 10 cm towards a 2 cm propane flame in a draught free enclosure. The distance the flame extended from the actuator orifice was determined from a linear scale mounted in the plane of the flame. Formulations containing strongly aggregated albuterol, or in which oleic acid remained undissolved were tested using continuous valves since these valves are less prone to blockage and the remaining formulations were tested using 63 μl metering valves. Except for the formulation containing 1% w/w ethanol in HFC-134a, all formulations containing a flammable component produced a measurable flame extension when sprayed into a propane flame. The flame was of extremely short duration in most cases, although formulations containing n-butane showed a tendency to burn slightly longer and had a small flame retreating to the actuator nozzle. Propellants containing propane tended to yield the longest flame extension. MDI gassing using flammable propellants is more difficult than using non-flammable CFCs, but is technically feasible.

FIG. 6 is a table showing the mean weight loss per actuation one hour and twenty four hours after filling each unit with a test formulation. Only test formulations in which albuterol was judged to be dispersed, and oleic acid dissolved are reported in FIGS. 6-7. Following priming (test firing after filling to fill the metering chamber with propellant), each MDI was weighed before and after ten actuations and the average weight loss per actuation was determined. The expected shot weight for those units which were fitted with a 63 μl metering valve was determined by multiplying the measured blend density (from FIGS. 1 and 2) of the test formulation by 63/1000. In many of the formulations (e.g., the HFC-134a/n-butane formulation), the observed shot weight was close to the expected value based on measured propellant density and valve metering volume. Moreover, the observed shot weight in many formulations did not alter appreciably over the 24 hour storage period.

FIG. 7 is a table showing the deposition results of albuterol sprayed into a cascade impactor for several aerosol units containing the test formulations. Each unit was fitted into the aerosol inlet port of an evaporation chamber located atop a calibrated cascade impactor (specifically, the Delron DCI-6 of Powell, Ohio), through which air was drawn at 12.45 liters/min, and discharged 10 times with shaking between each actuation. The procedure has been fully described in "Comparison of output particle size distributions from pressurized aerosols formulated as solutions and suspensions", Richard N. Dalby and Peter R. Byron, *Pharm. Res.*, 5, 36-39 (1988), and that article is hereby incorporated by reference. The actuator, evaporation chamber, each slide and the terminal filter of the impactor were washed with 50% volume in volume (v/v) aqueous methanol and analyzed for drug by high performance liquid chromatography (HPLC). Albuterol deposition in the actuator accounted for approximately 19% (standard deviation=4%) of the total emitted dose from all formulations. Deposition in the evaporation chamber was more variable, accounting for approximately 51% (standard deviation =6%) of the total emitted dose from all formulations. Evaporation chamber deposition is probably attributable to particles with aerodynamic diameters greater than 11.2 μm, and is likely to be indicative of particles or droplets which would impact in the mouth or oropharynx following inhalation. The percentage of the emitted dose reaching the cascade impactor following spraying of reformulated MDIs was compared to a control formulation (identified in FIG. 7 as "CFC-11/CFC-12") which contained albuterol and oleic acid in a 72% w/w CFC 12 and 28% w/w CFC-11 (a mixture commonly used in conventional CFC based MDIs). In comparison to this control, several reformulated MDIs produced more, or an equivalent fractional deposition within the impactor, where at least a proportion of the particles are expected to be respirable if inhaled. Particles within the impactor have an aerodynamic diameter less than 11.2 μm, which is similar to that claimed for Apparatus 1 in the British Pharmacopoeia where particles recovered from the second stage have an aerodynamic diameter of less than about 10 μm (see, *British Pharmacopoeia*, p. 875, appendix XVII C, A204-A207 (1988)).

Referring back to FIG. 6, the mean shot weight was observed to decrease markedly over the 24 hour storage period for some formulations, and the valve became stiff or failed to fire in certain aerosol units (e.g., CFC-12/isobutane, CFC-12/HCFC-123, and propane/HCFC-123). This stiffness resulted despite the fact that 0.2% weight in volume (w/v) oleic acid was completely dissolved in the propellant blend test formulations and should have provided adequate lubrication. Stiffness in the operation of the valve actuator may cause less than the expected volume of aerosol to be delivered, and this would account for the corresponding decrease in mean shot weight over the 24 hour time period. The inventors determined that stiff operation of the valve actuator could be the result of the propellants in the test formulations causing swelling of the nitrile seats positioned at the juncture of the valve actuator and pressurized aerosol container (nitrile seats were used with all the test aerosol units discussed above in conjunction with FIGS. 1-7).

FIG. 8 shows the weight gain of several elastomeric materials following immersion in a liquified propellant for 24 hours. Low density polyethylene (LDP), nitrile, chlorobutyl, black and white buna, butyl and neoprene are all commercially used gasket materials for aerosol containers. One preweighed seal of each type of elastomer was placed in a 20 ml aerosol bottle which was subsequently sealed using a continuous valve, and filled with liquified propellant through the valve. After 24 hours, the valve was removed and the seals reweighed as rapidly as possible. All propellants caused some degree of swelling in all elastomers tested, with the exception of perfluoropentane. After approximately one month the seals were weighed again. With the exception of nitrile rubber in dimethyl ether, which decreased in weight by 5%, all other elastomers returned to 100±2% of their initial weight after one month standing in air at ambient temperature.

FIG. 8 shows that all the elastomeric compounds tested, except chloro-butyl and butyl rubbers, showed only very limited swelling after twenty four hours of exposure to the alkane propellants (e.g., propane, n-butane, and isobutane). HFC-134a caused limited swelling of the LDP, chlorobutyl, butyl and neoprene gaskets, but caused a significant amount of swelling of the nitrile and black and white buna gaskets. Nitrile rubber was also found to be particularly affected by HCFC-123, which caused an approximately 400% increase in gasket weight. HCFC-123 also induced swelling of a similar magnitude in black and white buna gaskets. The nitrile rubber gasket which was immersed in dimethyl ether gave rise to a brown supernatant liquid after one month of standing in air at ambient temperature which is indicative of limited dissolution or leaching of significant amounts of extractables.

FIG. 9 shows the results of a second experiment where preweighed and premeasured nitrile elastomer gaskets placed in an aerosol bottle filled with a liquified propellant, as described above in conjunction with FIG. 8, and removed and rapidly weighed and measured after a twenty four hour period. Nitrile swelling and weight increase for gaskets placed in the alkane propellants was only slight and was of the same order of magnitude as that found with CFC-12 and CFC-114. The nitrile gaskets exposed to CFC-11, dimethyl ether and HCFC-123 all experienced an increase in length and a substantial percentage increase in weight. The nitrile gasket exposed to HFC-134a exhibited modest increases in length and weight. The nitrile gasket exposed to perfluoropentane had a slight decrease in length and no appreciable change in weight.

Some elastomer swelling is desirable for the MDI environment since the gasket provides a seal between the aerosol container and the valve actuator. Therefore, using perfluoropentane alone as a propellant in an MDI may not produce satisfactory results since, as is shown in FIGS. 8 and 9, no appreciable swelling occurred for any of the several elastomer gaskets examined. Too much elastomer swelling, as is the case for example when nitrile or black or white buna gaskets are exposed to either HCFC-123 or dimethyl ether (see FIGS. 8 and 9), is undesirable since this leads to stiff operation of the valve actuator (as discussed above in conjunction with FIG. 7). The results in FIGS. 8 and 9 show that the alkane and CFC propellants produce optimum results with a wide variety of elastomer materials. However, it should be understood that optimum elastomer swelling results can be achieved by combining propellants into blends.

For example, in the experiments reported in FIGS. 2-7, aerosol containers with nitrile gaskets were utilized. FIG. 6 shows that aerosol units filled with HFC-134a/iso-butane and HFC-134a/n-butane propellant blends had no appreciable decline in the mean shot weight per actuation twenty four hours after assembling the aerosol units and neither of these aerosol units experienced stiff operation of the valve actuator. Yet, FIGS. 8 and 9 show that nitrile gasket exposure to HFC-134a causes noticeable swelling within twenty four hours. Hence, the combination of an alkane propellant with HFC-134a may allow a nitrile gasket to be used in the MDI environment when HFC-134a is the high pressure propellant of choice. The inventors consider similar combinations of propellants, including combinations of three or more propellants, to achieve optimum elastomer swelling results to be within the scope of this invention. The propellants chosen for any particular blend will depend upon the type of elastomer seal used.

In the experiments, albuterol was used as the medicament; however, it should be understood that many other medicaments could be used with the inventive propellant blends. Albuterol is a white crystalline drug present as a micronized suspension and is typical of many other drugs delivered by MDIs. For pharmaceutical purposes, the particle size of the powder is preferably no greater than 100 microns in diameter, since larger particles may clog the metering valve or orifice of the container. Preferably, the particle size should be less than 10 microns in diameter. The concentration of medicament depends upon the desired dosage, but will generally be in the range 0.001 to 5% by weight. In addition, in the experiments oleic acid was used as the surfactant for dispersing the albuterol; however it should be understood that many different surfactants could be employed with the inventive propellant blends. As recently reported in Dalby et al., "CFC Propellant Substitution: P-134a as a Potential Replacement for P-12 in MDIs", *Pharm. Tech.*, March, 1990, pages 26 to 33, the percentage composition of each propellant constituent in a propellant blend required for completely dissolving a surfactant varies with the type of surfactant used and the weight percentage of the surfactant mixed into the propellant blend. Hence, the MDI application will influence the choice of surfactant and the final concentrations of propellants utilized. In most MDI formulations, surfactants will be present in amounts not exceeding five percent of the total formulation and are usually present in the weight ratio of 1:100 to 10:1 surface active agent:drug(s), but the surface active agent may exceed this weight ratio in cases where the drug concentration in the formulation is very low and be reduced below the ratio in certain cases where novel valve technology which reduces the requirement for valve lubrication is employed.

While the invention has been described in terms of its preferred embodiments wherein albuterol and oleic acid are either suspended in a formulation comprised of HFC-134a alone or HFC-134a blended with another propellant compound or suspended in a formulation comprised of a binary hydrocarbon blend, those skilled in the art will recognize that the medicament and surfactant chosen, the percentages of the propellant constituents in the HFC-134a and hydrocarbon blends, and the number of propellants used in the blend (e.g., binary, tertiary, and quaternary blends) can be varied within the spirit and scope of the appended claims.

Having thus described our invention, what we claim and desire to secure by Letters Patent is as follows:

1. A metered dose inhaler, comprising:
   a container capable of holding fluids under pressure;
   a valve connected to said container;
   gaskets associated with said valve selected from the group consisting of low density polyethylene, butyl elastomer, and neoprene; and
   an aerosol formulation positioned within said container, said aerosol formulation including a drug dissolved or dispersed in 1,1,1,2-tetrafluoroethane, said 1,1,1,2-tetrafluoroethane being the sold propellant of said aerosol formulation.

2. A metered dose inhaler, comprising:
   a container capable of holding fluids under pressure;
   a valve connected to said container;
   gaskets associated with said valve selected from the group consisting of low density polyethylene and chlorobutyl elastomer; and
   an aerosol formulation positioned within said container including a drug dissolved or dispersed in dimethyl ether.

3. A metered dose inhaler, comprising:
   a container capable of holding fluids under pressure;
   a valve connected to said container;
   nitrile gaskets associated with said valve; and
   an aerosol formulation positioned within said container including a drug dissolved or dispersed in a propellant blend including at least 1,1,1,2-tetrafluoroethane and an alkane propellant.

* * * * *